United States Patent
Rishi

(10) Patent No.: US 10,201,576 B2
(45) Date of Patent: Feb. 12, 2019

(54) HERBAL COMPOSITION FOR VAGINAL TREATMENT

(71) Applicant: Bhatia Rishi, New Mumbai (IN)

(72) Inventor: Bhatia Rishi, New Mumbai (IN)

(73) Assignee: Ultratech India Limited, New Mumbai (IN)

( * ) Notice: Subject to any disclaimer, the term of this patent is extended or adjusted under 35 U.S.C. 154(b) by 834 days.

(21) Appl. No.: 14/401,582

(22) PCT Filed: May 20, 2013

(86) PCT No.: PCT/IN2013/000323
§ 371 (c)(1),
(2) Date: Nov. 17, 2014

(87) PCT Pub. No.: WO2013/175504
PCT Pub. Date: Nov. 28, 2013

(65) Prior Publication Data
US 2015/0157674 A1    Jun. 11, 2015

(30) Foreign Application Priority Data

May 18, 2012 (IN) .......................... 1519/MUM/2012

(51) Int. Cl.
| | | |
|---|---|---|
| A61K 36/23 | (2006.01) | |
| A61K 36/185 | (2006.01) | |
| A61K 49/00 | (2006.01) | |
| A61K 9/00 | (2006.01) | |
| A61K 47/10 | (2017.01) | |
| A61K 47/12 | (2006.01) | |
| A61K 9/06 | (2006.01) | |
| A61K 47/32 | (2006.01) | |

(52) U.S. Cl.
CPC ............ *A61K 36/23* (2013.01); *A61K 9/0034* (2013.01); *A61K 9/06* (2013.01); *A61K 36/185* (2013.01); *A61K 47/10* (2013.01); *A61K 47/12* (2013.01); *A61K 47/32* (2013.01)

(58) Field of Classification Search
CPC .. A61K 2300/00; A61K 36/185; A61K 36/23; A61K 47/10; A61K 47/12; A61K 47/32; A61K 9/0034; A61K 9/06; C12Q 1/025
See application file for complete search history.

(56) References Cited

U.S. PATENT DOCUMENTS

| | | | | |
|---|---|---|---|---|
| 5,766,636 A | * | 6/1998 | Turk | A61K 9/2013 424/488 |
| 8,883,137 B2 | * | 11/2014 | Yu | A23L 1/3016 424/93.51 |
| 2001/0055625 A1 | | 12/2001 | Katiyar et al. | |
| 2003/0170326 A1 | * | 9/2003 | Qazi | A61K 31/12 424/734 |
| 2004/0022875 A1 | | 2/2004 | Das et al. | |
| 2007/0258913 A1 | * | 11/2007 | Rossel | A61K 31/122 424/49 |
| 2009/0035361 A1 | | 2/2009 | Schiena | |
| 2009/0310839 A1 | * | 12/2009 | Katzenelson | C12Q 1/025 382/128 |

FOREIGN PATENT DOCUMENTS

DE    19625560 A1 *  1/1998  ........... A61K 8/0254

OTHER PUBLICATIONS

Mironava T; Hadjiargyrou M; Simon M; Jurukovski V; Rafailovich MH. "Gold nanoparticles cellular toxicity and recovery: effect of size, concentration and exposure time" Nanotoxicology. Mar. 2010, 4(1),p. 120-37. doi: 10.3109/17435390903471463.*
Tallarida, R.J., "Combinations of Chemicals" and "Calculations for Combination Drug Analysis", Drug Synergism and Dose-Effect Analysis, Chapman & Hall/CRC, 2000, chapters 1 and 4, pp. 1-13 and 57-71. (Year: 2000).*
DrRubidium "18 Again: Vaginal tightening . . . " <URL:thirtyseven. scientopia.org/2012/12/06/the-breakdown-18-again/>, Dec. 6, 2012,18 pages. (Year: 2012).*
International Patent Search Report for PCT/IN2013/000323, dated Nov. 22, 2013, 6 pages.

* cited by examiner

*Primary Examiner* — Aaron J Kosar
(74) *Attorney, Agent, or Firm* — Veritay Group IP; Susan B. Fentress

(57) ABSTRACT

The present invention discloses a herbal formulation comprising therapeutic effective amount of plant extract of *Woodfordia Floribunda*; therapeutic effective amount of plant extract of *Centella Asiatica*; and an effective amount of at least one pharmaceutically acceptable excipient.

13 Claims, No Drawings

HERBAL COMPOSITION FOR VAGINAL TREATMENT

CROSS REFERENCE TO RELATED APPLICATIONS

This application is a § 371 National Stage Application of PCT/IN2013/000323filed 20 May 2013 which claims priority to IN 1519/MUM/2012 filed 18 May 2012(hereby specifically incorporated by reference).

Technical Field Of Invention

The present invention relates to formulation comprising herbal extracts for the treatment and prevention of vaginal conditions and diseases. More specifically, the invention relates to herbal formulation comprising therapeutic effective amount of *Woodfordia floribunda* plant extract; therapeutic effective amount of *Centella asiatica* plant extract and effective amount of at least one pharmaceutically acceptable excipient for treatment of vaginal conditions, in particular for vaginal tightening and rejuvenation.

Background And Prior Art

The vaginal tissue is stretched during vaginal child birth; the effects of which may be permanent and women tend to have medical consequences. Vaginal tissues also tend to weaken and lose their tonicity with age, local traumas, chronic infections, hormonal imbalance due to malnutrition and genetic disorders. The vagina becomes flaccid in such conditions and this can negatively interfere with the sexual response.

A loosened state of the vagina can contribute to female sexual dysfunction as natural swelling and lubrication of the vagina that occurs during an arousal phase of an intercourse may take longer to occur in the loosened state. Examples of problems related to female sexual dysfunction include, but are not limited to, a loosened, relaxed, stretched, prolapsed or atrophied state of vagina; loss of sexual arousal; pain or discomfort during intercourse (dyspareunia); diminished blood flow to the vagina and the genital area; inability to achieve orgasm and general sexual dissatisfaction.

Further, beyond the loss of sexual satisfaction, if the problem is left untreated, it can give rise to several health risks in future life. The woman may develop a feeling of frustration, a loss of self-esteem and anxiety, lack of desire, urinary incontinence and formation of unpleasant genital odour among the other side effects due to persistent condition of loosened vaginal tissue.

To address these above-described vaginal conditions and problems related to female sexual dysfunction, various gels, creams, drops, suppositories, aerosol, oil, ointment, serum for intra vaginal application have been developed. Continuous research is ongoing to develop improved compositions which provide beneficial vaginal treatment properties for a wide variety of vaginal disorders. However; there is still a need to develop a formulation having minimal side effects and also which is more efficacious than the products known in the art.

Further, the beneficial effect of extracts of herbs and other natural plant ingredients are also recognized in vaginal muscle care. Herbal remedies, are particularly desired by consumers as they are clinically proven to be safe, highly effective, and do not exhibit any side effects.

The use of papain, Lavender oil, Galactoarabinan, Magnesium Aluminum Silicate, Sweet Almond Oil, Sesame Oil, Butylene Glycol, *Phyllanthus emblica* fruit extract, urea, allantoin, vitamin C, tocotrienols, ubiquinone, pomegranate, colloidal gold, Tocopheryl Acetate (Vitamin E Acetate), Panthenol (Vitamin B5), etc. have been known for use in compositions for topical applications for the treatment of vaginal conditions.

Surgical procedures are also known for the treatment of vaginal conditions. Alternatively, various vaginal procedures such as vaginal tightening rejuvenation surgery etc exist for the treatment of the loosened state and other such abnormalities of the vagina. However, such surgery also implicates pain, involves high cost and potential complications, including infection, altered sensation, dyspareunia, adhesions, and scarring. Further, due to safety concerns, such vaginal procedures have become quite unpopular. (See, for example, Committee Opinion #378 of the American College of Obstetricians and Gynecologists, entitled "Vaginal Rejuvenation and Cosmetic Vaginal Procedures", published in the September 2007 issue of Obstetrics & Gynecology).

Hence, there is a need to develop a herbal gel formulation for vaginal application, that can be manufactured in a cost effective manner and has minimal side effects along with superior anti-oxidizing, anti-aging, muscle tightening, antimicrobial, anti-inflammatory, integument, vaginal-supporting, and regenerative stimulating effect that can provide multi-faceted protection, treatment and prevention in a wide variety of vaginal conditions.

Alternatively, there is a need to effectively increase female sexual response and preventing female sexual dysfunction to create satisfactory sexual experiences for a woman and her partner. There is a need for providing moisturizing, toning and replenishing effects for vaginal rejuvenation and vaginal lubrication in women, in an effective and a hygienic manner. Moreover, there is a need for providing herbal formulation with antimicrobial effects for preventing and controlling microbial infections in vaginal conditions.

SUMMARY OF THE INVENTION

Surprisingly, the inventors have found that, herbal formulation comprising:
  a. a therapeutic effective amount of *Woodfordia floribunda* plant extract;
  b. a therapeutic effective amount of *Centella asiatica* plant extract; and,
  c. an effective amount of at least one pharmaceutically acceptable excipient; is effective for treatment of vaginal conditions.

The present invention also relates to herbal formulation in the form of a gel.

The present invention also relates to the process for preparation of the herbal formulation comprising the steps of:
a) preparing aqueous plant extracts of *Woodfordia floribunda* and *Centella asiatica* in DM water;
b) stirring gelling agent soaked in DM water and adjusting pH of the solution; and
c) mixing the plant extract of step (a) and the solution of step (b) along with at least one pharmaceutically acceptable excipient under continuous stirring to obtain required herbal gel formulation.

It has also been found that the herbal formulation of the present invention showed enhanced efficacy in treating vaginal conditions when compared to the individual formulations.

This and other objects are attained in accordance with the present invention wherein there are provided several embodiments for preparing herbal formulation comprising the plant extracts.

DETAILED DESCRIPTION OF THE INVENTION

In describing the embodiments of the invention, specific terminology is resorted for the sake of clarity. However, it is not intended that the invention be limited to the specific terms so selected and it is to be understood that each specific term includes all technical equivalents that operate in a similar manner to accomplish a similar purpose.

The invention relates to herbal formulation comprising of:
  a) a therapeutic effective amount of *Woodfordia floribunda* plant extract;
  b) a therapeutic effective amount of *Centella asiatica* plant extract; and,
  c) an effective amount of at least one pharmaceutically acceptable excipient.

According to an embodiment, *Woodfordia floribunda* plant extract is present in the range of 0.1% to 5% w/w of the total composition.

According to another embodiment, *Centella asiatica* plant extract is present in the range of 0.1% to 5% w/w of the total composition.

According to one of the embodiment, the pharmaceutically acceptable excipient can include one or more astringents, antioxidants, vaginal conditioning agents, vasodilating agents, thickening agents, preservatives, flavouring agents, lubricating agents, vitality imparter, colorants and water. However, those skilled in the art will appreciate that it is possible to utilize additional pharmaceutically acceptable excipients without departing from the scope of the present invention.

According to an embodiment, the pharmaceutically acceptable excipient is present in the range of 90% to 98% w/w of the total composition.

According to another embodiment, the pharmaceutically acceptable excipient includes at least one astringent such as potassium aluminum sulphate (alum), extract of *Punica granatum, Acacia senegal, Andrographis paniculata, Curcuma comosa, Aancyelus pyrethrum* (anar kara), Shilajit or combination thereof. The astringent is present in the range of 0.01% to 5.0% w/w of the total composition.

According to yet another embodiment, the pharmaceutically acceptable excipient includes at least one antioxidant such as Vitamin E, Vitamin C, Gold nanoparticles or combination thereof. The antioxidant is present in the range of 0.01% to 0.5% w/w of the total composition.

According to further another embodiment, the pharmaceutically acceptable excipient includes at least one vaginal conditioning agent such as Aloe vera, almond extract, propylene glycol, *Aloe barbadensis, Tinospora cordifolia,* Shilajit, glycols, glycerine, sorbitol or combination thereof. The vaginal conditioning agent is present in the range of 0.50% to 5% w/w of the total composition.

According to another embodiment, the pharmaceutically acceptable excipient can optionally include vasodilating agent can be an extract of at least one plant such as *Butea frondosa, Myristica fragrans, Asparagus racemosus, Butea monosperma, Acorus callomus* and *Withinia somnifera*. The vasodilating agent can be in a range from 1% to 5% w/w of the total composition.

According to further embodiment, the pharmaceutically acceptable excipient includes at least one thickening agent such as carbomer, sodium carboxymethylcellulose, gelatin or combination thereof. The thickening agent is present in the range of 0.5-1.5% w/w of the total composition.

According to yet another embodiment, the pharmaceutically acceptable excipient includes at least one preservative such as sodium benzoate, potassium sorbate, sodium methyl paraben, propyl paraben, benzoic acid, sodium metabisulfite, disodium EDTA, butyl paraben, chlorobutanol or combination thereof. The preservative is present in the range of 0.01-2.0% w/w of the total composition.

According to another embodiment, the pharmaceutically acceptable excipient includes a lubricating agent such as sesame oil, propylene glycol, almond oil or combination thereof. The lubricating agent is present in the range of 0.01% to 5% w/w of the total composition.

According to one of the embodiment, the pharmaceutically acceptable excipient can optionally include a vitality imparter such as gold, gold glitter and gold fine particles. The vitality imparter can be in the range of 0.01-0.05% w/w of the total composition.

According to another embodiment, the pharmaceutically acceptable excipient can optionally include a colorant such as gold colour. The colorant can be in the range of 0.01%-0.04% w/w of the total composition.

According to yet another embodiment, the pharmaceutically acceptable excipient includes flavouring agent such as apricot, vanilla, cane, berry, green apple, almond, honey and rose. The flavouring agent is present in the range of 0.01% to 0.05% w/w of the total composition.

According to another embodiment, water is present in the range of 0.01% to 90% w/w of the total composition.

According to an embodiment, the herbal formulation comprises therapeutic effective amount of *Woodfordia floribunda* plant extract, therapeutic effective amount of *Centella asiatica* plant extract, effective amount of potassium aluminum sulphate (alum), an effective amount of gold nanoparticles and effective amount of at least one pharmaceutically acceptable additive.

According to an embodiment, the herbal formulation comprises therapeutic effective amount of *Woodfordia floribunda* plant extract, therapeutic effective amount of *Centella asiatica* plant extract, effective amount of Aloe vera, effective amount of Almond, effective amount of *Punica granatum*, effective amount of potassium aluminum sulphate (alum), effective amount of Gold, effective amount of Vitamin E and effective amount of at least one pharmaceutically acceptable additive.

According to yet another embodiment of the invention the herbal formulation may be formulated as a gel, cream, drop, suppository, aerosol, oil, ointment or serum. The formulation is preferably in the form of a gel.

According to one embodiment, the herbal formulation comprising therapeutic effective amount of *Woodfordia floribunda* plant extract; therapeutic effective amount of *Centella asiatica* plant extract and effective amount of at least one pharmaceutically acceptable excipient is a water-based formulation for use as a topical application.

According to a further embodiment, the herbal formulation comprising therapeutic effective amount of *Woodfordia floribunda* plant extract; therapeutic effective amount of *Centella asiatica* plant extract; and effective amount of at least one pharmaceutically acceptable excipient is used as a vaginal care composition.

According to a still further embodiment, the herbal formulation comprising therapeutic effective amount of *Woodfordia floribunda* plant extract; therapeutic effective amount of *Centella asiatica* plant extract; and effective amount of at least one pharmaceutically acceptable excipient is used as an inter-vaginal composition.

According to one of the preferred embodiment, the process for preparation of the herbal formulation comprises of:
a) preparing aqueous plant extracts of *Woodfordia floribunda* and *Centella asiatica* in DM water;
b) stirring gelling agent soaked in DM water and adjusting pH of the solution; and
c) mixing the plant extract of step (a) and the solution of step (b) along with at least one pharmaceutically acceptable excipient under continuous stirring to obtain required herbal formulation.

According to another preferred embodiment, the process for preparation of the herbal formulation comprises of:
a) preparing plant extract from the whole plant or one or more parts of the plant by placing 500 gms of the plant in 500 ml Distill water (DM) water in mortar, grinding the same thoroughly with the pestle and filtering it;
b) stirring the gelling agent soaked in water for 30-35 min and adjusting the pH by adding
Sodium hydroxide solution to obtain uniform composition;
c) adding antioxidant, preservatives dissolved in lubricating agent in step (b) and stirring for 20-25 minutes;
d) mixing the extract of step (a) with solution of step (c) under stirring for 10 minutes on each plant extract addition;
e) adding astringent and conditioning agent under stirring for 10-15 minutes; and
f) adding vitality imparter, flavoring agent and colorant under stirring for 10-15 minutes to obtain required herbal formulation.

According to another embodiment, the invention further relates to a method of application of the herbal formulation comprising effective amount of plant extract of *Woodfordia floribunda* plant; effective amount of extract of *Centella asiatica* plant; and effective amount of at least one pharmaceutically acceptable excipient.

According to another embodiment, the invention further relates to a method of treating vaginal conditions in female subjects. This method comprises administering to the female subject suffering from vaginal disorder, an effective amount of the herbal formulation comprising of a therapeutically effective amount of plant extract of *Woodfordia floribunda* plant; a therapeutically effective amount of extract of *Centella asiatica* plant; and an effective amount of at least one pharmaceutically acceptable excipient.

According to yet another embodiment, the herbal formulation of the invention is not only effective for vaginal treatment composition but also acts as an effective antioxidant, antiseptic and a lubricant in other vaginal conditions. The herbal formulation also plays an important role in the firming, tightening and for rejuvenation of the vagina.

According to another embodiment, the herbal formulation effectively heals wounds and increases vascularization of the connective tissues in other skin conditions.

From the foregoing it will be observed that numerous modifications and variations can be effectuated without departing from the true spirit and scope of the novel concepts of the present invention. It is to be understood that no limitation with respect to the specific embodiments illustrated is intended or should be inferred.

The following non-limiting examples illustrate the herbal formulation for vaginal treatment.

EXAMPLE 1

Preparation of Herbal Formulation for Vaginal Treatment

The process for preparation of the herbal formulation comprises of:
(a) preparing plant extract by placing separately whole plant or one or more parts of *Woodfordia floribunda* (7.5 gms), *Centella asiatica* (7.5 gms), *Punica granatum* (7.5 gms) and DM water in mortar, grinding thoroughly with the pestle and filtering it;
(b) Stirring the Carbomer (12.5 gms) soaked in DM water (850 ml) for 30-35 min and adjusting the pH by adding Sodium hydroxide solution (2.5 gms in 40 ml water) to obtain uniform composition;
(c) adding Alum (0.4 gms), Sodium benzoate (3.8 gms) and Potassium Sorbate (1.5 gms) dissolved in Propylene Glycol (30.4 ml) in step (b) and stirring for 10-15 minutes;
(d) mixing the extract of step (a) with formulation of step (c) under stirring for 10 minutes on each plant extract addition;
(e) adding Almond (1.5 gms), and Aloe vera (1.5 gms) under stirring for 10-15 minutes; and
(f) adding Vitamin E (0.2 gms), flavoring agent and gold (0.2 gms each) under stirring for 10-15 minutes to obtain required herbal gel formulation.

TABLE 1

Ingredients used in herbal formulation comprising

| Sr. No. | Component | Amount used % w/w |
|---|---|---|
| 1 | *Woodfordia floribunda* | 0.75 |
| 2 | *Centella asiatica* | 0.75 |
| 3 | *Punica granatum* | 0.75 |
| 4 | Alum | 0.04 |
| 5 | Almond | 1.5 |
| 6 | Aloe vera | 1.5 |
| 7 | Propylene Glycol | 3.04 |
| 8 | Carbomer | 1.25 |
| 9 | Sodium hydroxide | 0.25 |
| 10 | Sodium benzoate | 0.38 |
| 11 | Potassium Sorbate | 0.15 |
| 12 | Vitamin E | 0.02 |
| 13 | Gold | 0.02 |
| 14 | Flavor | 0.02 |
| 15 | DM Water | Q.S. |

EXAMPLE 2

Preparation of Herbal Formulation for Vaginal Treatment

The process for preparation of the herbal formulation comprises of:
(a) preparing plant extract by placing separately whole plant or one or more parts of *Woodfordia floribunda* (1 gms), *Centella asiatica* (1 gms), *Punica granatum* (1 gms) and DM water in mortar, grinding thoroughly with the pestle and filtering it;
(b) Stirring the Carbomer (12.5 gms) soaked in DM water (850 ml) for 30-35 min and adjusting the pH by adding Sodium hydroxide solution (2.5 gms in 40 ml water) to obtain uniform composition;
(c) adding Alum (0.4 gm), Sodium benzoate (3.8 gms) and Potassium Sorbate (1.5 gms) dissolved in Propylene Glycol (30.4 ml) in step (b) and stirring for 15-20 minutes;

(d) mixing the extract of step (a) with formulation of step (c) under stirring for 10 minutes on each plant extract addition;
(e) adding Almond (1.5 gms), and Aloe vera (1.5 gms) under stirring for 10-15 minutes; and
(f) adding Vitamin E (0.2 gms), flavoring agent and gold (0.2 gms each) under stirring for 10-15 minutes to obtain required herbal gel formulation.

TABLE 2

Ingredients used in herbal formulation comprising

| Sr. No. | Component | Amount used % w/w |
|---|---|---|
| 1 | *Woodfordia floribunda* | 0.1 |
| 2 | *Centella asiatica* | 0.1 |
| 3 | *Punica granatum* | 0.1 |
| 4 | Alum | 0.04 |
| 5 | Almond | 1.5 |
| 6 | Alovera | 1.5 |
| 7 | Propylene Glycol | 3.04 |
| 8 | Carbomer | 1.25 |
| 9 | Sodium hydroxide | 0.25 |
| 10 | Sodium benzoate | 0.38 |
| 11 | Potassium Sorbate | 0.15 |
| 12 | Vitamin E | 0.02 |
| 13 | Gold | 0.02 |
| 14 | Flavor | 0.02 |
| 15 | DM Water | Q.S. |

EXAMPLE 3

Preparation of Herbal Formulation for Vaginal Treatment

The process for preparation of the herbal formulation comprises of:
(a) preparing plant extract by placing separately whole plant or one or more parts of *Woodfordia floribunda* (50 gms), *Centella asiatica* (7.5 gms), *Punica granatum* (20 gms) and DM water in mortar, grinding thoroughly with the pestle and filtering it;
(b) Stirring the Carbomer (12.5 gms) soaked in DM water (850 ml) for 30-35 min and adjusting the pH by adding Sodium hydroxide solution (2.5 gms in 40 ml water) to obtain uniform composition;
(c) adding Alum (10 gm), Sodium benzoate (3.8 gms) and Potassium Sorbate (1.5 gms) dissolved in Propylene Glycol (30.4 ml) in step (b) and stirring for 15-20 minutes;
(d) mixing the extract of step (a) with formulation of step (c) under stirring for 10 minutes on each plant extract addition;
(e) adding Almond (5 gms), and Aloe vera (5 gms) under stirring for 10-15 minutes; and
(f) adding Vitamin E (2.5 gms), flavoring agent and gold (0.2 gms each) under stirring for 10-15 minutes to obtain required herbal gel formulation.

TABLE 3

Ingredients used in herbal formulation comprising

| Sr. No. | Component | Amount used % w/w |
|---|---|---|
| 1 | *Woodfordia floribunda* | 5 |
| 2 | *Centella asiatica* | 0.75 |
| 3 | *Punica granatum* | 2 |
| 4 | Alum | 1 |
| 5 | Almond | 0.5 |

TABLE 3-continued

Ingredients used in herbal formulation comprising

| Sr. No. | Component | Amount used % w/w |
|---|---|---|
| 6 | Alovera | 0.5 |
| 7 | Propylene Glycol | 3.04 |
| 8 | Carbomer | 1.25 |
| 9 | Sodium hydroxide | 0.25 |
| 10 | Sodium benzoate | 0.38 |
| 11 | Potassium Sorbate | 0.15 |
| 12 | Vitamin E | 0.25 |
| 13 | Gold | 0.02 |
| 14 | Flavor | 0.02 |
| 15 | DM Water | Q.S. |

EXAMPLE 4

Preparation of Herbal Formulation for Vaginal Treatment

The process for preparation of the herbal formulation comprises of:
(a) preparing plant extract by placing separately whole plant or one or more parts of *Woodfordia floribunda* (7.5 gms), *Centella asiatica* (50 gms), *Punica granatum* (15 gms) and DM water in mortar, grinding thoroughly with the pestle and filtering it;
(b) Stirring the Carbomer (12.5 gms) soaked in DM water (850 ml) for 30-35 min and adjusting the pH by adding Sodium hydroxide solution (2.5 gms in 40 ml water) to obtain uniform composition;
(c) adding Alum (5 gm), Sodium benzoate (3.8 gms) and Potassium Sorbate (1.5 gms) dissolved in Propylene Glycol (30.4 ml) in step (b) and stirring for 15-20 minutes;
(d) mixing the extract of step (a) with formulation of step (c) under stirring for 10 minutes on each plant extract addition;
(e) adding Almond (5 gms), and Aloe vera (1.5 gms) under stirring for 10-15 minutes; and
(f) adding Vitamin E (0.2 gms), flavoring agent and gold (0.2 gms each) under stirring for 10-15 minutes to obtain required herbal gel formulation.

TABLE 4

Ingredients used in herbal formulation comprising

| Sr. No. | Component | Amount used % w/w |
|---|---|---|
| 1 | *Woodfordia floribunda* | 0.75 |
| 2 | *Centella asiatica* | 5 |
| 3 | *Punica granatum* | 1.5 |
| 4 | Alum | 0.5 |
| 5 | Almond | 0.5 |
| 6 | Alovera | 1.5 |
| 7 | Propylene Glycol | 3.04 |
| 8 | Carbomer | 1.25 |
| 9 | Sodium hydroxide | 0.25 |
| 10 | Sodium benzoate | 0.38 |
| 11 | Potassium Sorbate | 0.15 |
| 12 | Vitamin E | 0.02 |
| 13 | Gold | 0.02 |
| 14 | Flavor | 0.02 |
| 15 | DM Water | Q.S. |

EXAMPLE 5

Preparation of Herbal Formulation for Vaginal Treatment

The process for preparation of the herbal formulation comprises of:
(a) preparing plant extract by placing separately whole plant or one or more parts of *Woodfordia floribunda* (15 gms), *Centella asiatica* (15 gms), *Punica granatum* (5 gms) and DM water in mortar, grinding thoroughly with the pestle and filtering it;
(b) Stirring the Carbomer (12.5 gms) soaked in DM water (850 ml) for 30-35 min and adjusting the pH by adding Sodium hydroxide solution (2.5 gms in 40 ml water) to obtain uniform composition;
(c) adding Alum (0.4 gms), Sodium benzoate (3.8 gms) and Potassium Sorbate (1.5 gms) dissolved in Propylene Glycol (30.4 ml) in step (b) and stirring for 15-20 minutes;
(d) mixing the extract of step (a) with formulation of step (c) under stirring for 10 minutes on each plant extract addition;
(e) adding Aloe vera (15 gms) under stirring for 10-15 minutes; and
(f) adding Vitamin E (0.2 gms), flavoring agent and gold (0.2 gms each) under stirring for 10-15 minutes to obtain required herbal formulation.

TABLE 5

Ingredients used in herbal formulation comprising

| Sr. No. | Component | Amount used % w/w |
|---|---|---|
| 1 | *Woodfordia floribunda* | 1.5 |
| 2 | *Centella asiatica* | 1.5 |
| 3 | *Punica granatum* | 0.5 |
| 4 | Alum | 0.04 |
| 5 | Almond | 0 |
| 6 | Alovera | 1.5 |
| 7 | Propylene Glycol | 3.04 |
| 8 | Carbomer | 1.25 |
| 9 | Sodium hydroxide | 0.25 |
| 10 | Sodium benzoate | 0.38 |
| 11 | Potassium Sorbate | 0.15 |
| 12 | Vitamin E | 0.02 |
| 13 | Gold | 0.02 |
| 14 | Flavor | 0.02 |
| 15 | DM Water | Q.S. |

EXAMPLE 6

A Clinical Study to Evaluate the Efficacy, Safety and Tolerability of Herbal Gel Formulation According to an Embodiment of the Invention [Test Product] Vs. Placebo in Females with Vaginal Relaxation Study Objectives:
Primary Objective:—
 To evaluate the efficacy of Test Product vs. Placebo in Females with Vaginal Relaxation.
Secondary Objective:—
 To evaluate the safety and tolerability of Test Product vs. Placebo in Females with Vaginal Relaxation.
 Global assessment of study medications.
Treatment:
 Test product—herbal formulation in accordance with an embodiment of the invention was applied 2 g once a day for period of 12 weeks in females with vaginal relaxation, Visits were scheduled as baseline visit (Visit 1) i.e. (day 1), Visit 2 (4th week), Visit 3 (8th week) and Visit 4 (12th week) after randomization to assess safety and efficacy.

Placebo was applied 2 g once a day for period of 12 weeks in females with vaginal relaxation, Visits were scheduled as baseline visit (Visit 1) i.e. (day 1), Visit 2 (4th week), Visit 3 (8th week) and Visit 4 (12th week) after randomization to assess safety and efficacy.

Efficacy and Safety Measurements:
The efficacy of the composition was evaluated on the basis of investigation of following parameters on Baseline visit (Visit 1) i.e. day 1 followed by visit 2 (4th week), visit 3 (8th week) and by the end of the therapy on visit 4 (12th week).

Improvement was Assessed by Questionnaires Administered Included Two Likert-Type Visual Analog Scale Questionnaires for Scoring Patient Reported for Vaginal Laxity/Looseness, Sexual Satisfaction were Graded as Follows:

Vaginal Laxity/Looseness
The observations were graded as follows:
1—Very Loose
2—Moderately Loose
3—Slightly Loose
4—Neither Tight nor Loose
5—Slightly Tight
6—Moderately tight
7—Very Tight

TABLE 6 (a)

| | Mean score (±std deviation) | |
|---|---|---|
| Duration | Test product | Placebo |
| Before pregnancy | 4.86 | 4.95 |
| Pre-treatment | 2.38 | 2.22 |
| Week 4 | 3.53 | 2.17 |
| Week 8 | 3.84 | 2.38 |
| Week 12 | 4.59 | 2.41 |

Sexual Satisfaction
The observations were graded as follows:
0—None
1—Poor
2—Fair
3—Good
4—Very Good
5—Excellent

TABLE 6 (b)

| | Mean score (±std deviation) | |
|---|---|---|
| Duration | Test product | Placebo |
| Before pregnancy | 4.24 | 4.20 |
| Pre-treatment | 2.03 | 2.00 |
| Week 4 | 3.20 | 2.07 |
| Week 8 | 3.67 | 2.14 |
| Week 12 | 3.98 | 2.20 |

Female Sexual Function Index (Questionnaire)
The observations were graded as follows:
1—Very low or none at all
2—Low
3—Moderate
4—High
5—Very high TABLE 6 (c)

| Duration | Mean score (±std deviation) | |
| --- | --- | --- |
| | Test product | Placebo |
| Pre-treatment | 3.08 | 3.12 |
| Week 4 | 6.39 | 3.37 |
| Week 8 | 6.68 | 3.53 |
| Week 12 | 8.11 | 3.71 |

Symptoms of Vaginal Infections Like Vaginal Itching, Vaginal Discharge, Odour, Inflammation, Burning Pain were Evaluated; However Results of Vaginal Itching are Provided Below:

The observations were graded as follows:

0—None

1—Mild

2—Moderate

3—Severe

TABLE 6 (d)

| Duration | Mean score (±std deviation) | |
| --- | --- | --- |
| | Test product | Placebo |
| Pre-treatment | 1.86 | 1.89 |
| Week 4 | 1.17 | 1.49 |
| Week 8 | 0.59 | 1.54 |
| Week 12 | 0.23 | 1.43 |

CONCLUSION

Surprisingly, the herbal formulation of the present invention comprising of *Woodfordia floribunda* plant extract and *Centella asiatica* plant extract along with at least one pharmaceutically acceptable carriers or excipient showed persistence of significant effect upto the end of the treatment i.e. 12 weeks post treatment.

The efficacy parameters such as Vaginal Laxity/looseness; Sexual Satisfaction; Female Sexual Function Index; Symptoms of Vaginal Infections such as vaginal itching; vaginal discharge; odour; inflammation and burning pain were evaluated on the basis of ratings by the patients, which showed a significant results in the group treated with herbal formulation according to an embodiment of the invention [test product] than to the group treated with placebo that showed very less result.

Further, the degree of improvement in terms of percentage improvement in vaginal laxity, sexual satisfaction, desire, arousal, lubrication, orgasm, overall satisfaction, pain, vaginal itching, vaginal discharge, odour, inflammation, burning pain; observed as per investigator and patient evaluation was 81%, 82%, 76%, 79%, 76%, 78%, 84%, 79%, 81%, 76%, 81%, 79% and 76% respectively in the test product group.

No significant improvement was observed in placebo group. Only group with Test product showed significant improvement compared to initial value.

Also, there were no adverse reactions observed in both the test product group i.e. herbal gel formulation according to an embodiment of the invention and in the placebo group.

Moreover, the safety of the composition was also evaluated and there were no adverse events observed during the study.

EXAMPLE 7

Comparison of Efficacy Study of the Herbal Formulation According to an Embodiment of the Present Invention Vis-à-Vis Prior Art Product Comprising Combination of *Pueraria mirifica; Quercus Infectoria* Gall Extract; *Hamamelis virginiana* and *Panax Ginseng* {Marketed Under the Brand Name INTIVAR} was Evaluated Based on Similar Criteria Such as Vaginal Laxity/Looseness, Sexual Satisfaction and Vaginal Infection Study Objectives:

Primary Objective:—

To evaluate the efficacy of Test Product vs. Prior art Product in Females with Vaginal Relaxation.

Secondary Objective:—

To evaluate the safety and tolerability of Test Product vs. Prior art Product in Females with Vaginal Relaxation.

Global assessment of study medications.

Treatment:

Test product—herbal formulation in accordance with an embodiment of the invention was applied 2 g once a day for period of 12 weeks in females with vaginal relaxation, Visits were scheduled as baseline visit (Visit 1) i.e. (day 1), Visit 2 ($4^{th}$ week), Visit 3 ($8^{th}$ week) and Visit 4 ($12^{th}$ week) after randomization to assess safety and efficacy.

Prior art Product was applied 2 g once a day for period of 12 weeks in females with vaginal relaxation, Visits were scheduled as baseline visit (Visit 1) i.e. (day 1), Visit 2 ($4^{th}$ week), Visit 3 ($8^{th}$ week) and Visit 4 ($12^{th}$ week) after randomization to assess safety and efficacy.

Efficacy and Safety Measurements:

The efficacy of the composition was evaluated on the basis of investigation of following parameters on Baseline visit (Visit 1) i.e. day 1 followed by visit 2 ($4^{th}$ week), visit 3 ($8^{th}$ week) and by the end of the therapy on visit 4 ($12^{th}$ week).

Improvement was Assessed by Questionnaires Administered Included Two Likert—Type Visual Analog Scale Questionnaires for Scoring Patient Reported for Vaginal Laxity/Looseness, Sexual Satisfaction were Graded as Follows:

Vaginal Laxity/Looseness

The observations were graded as follows:

1—Very Loose

2—Moderately Loose

3—Slightly Loose

4—Neither Tight nor Loose

5—Slightly Tight

6—Moderately tight

7—Very Tight

TABLE 7 (a)

COMPARISON OF MEAN SCORE OF IMPROVEMENT IN VAGINAL LAXITY/LOOSENESS

| Duration | Mean score (±std deviation) | |
| --- | --- | --- |
| | Test product | Prior art Product |
| Before pregnancy | 4.55 | 4.73 |
| Pre-treatment | 2.39 | 2.34 |
| Week 4 | 3.07 | 2.73 |

TABLE 7 (a)-continued

COMPARISON OF MEAN SCORE OF IMPROVEMENT IN VAGINAL LAXITY/LOOSENESS

| Duration | Mean score (±std deviation) | |
|---|---|---|
| | Test product | Prior art Product |
| Week 8 | 3.55 | 3.05 |
| Week 12 | 3.98 | 3.45 |

Sexual Satisfaction

The observations were graded as follows:

0—None
1—Poor
2—Fair
3—Good
4—Very Good
5—Excellent

TABLE 7 (b)

COMPARISON OF MEAN SCORE FOR SEXUAL SATISFACTION

| Duration | Mean score (±std deviation) | |
|---|---|---|
| | Test product | Prior art Product |
| Before pregnancy | 4.24 | 4.20 |
| Pre-treatment | 2.03 | 2.00 |
| Week 4 | 3.20 | 2.24 |
| Week 8 | 3.67 | 2.74 |
| Week 12 | 3.98 | 3.20 |

Female Sexual Function Index (Questionnaire)

The observations were graded as follows:

1—Very low or none at all
2—Low
3—Moderate
4—High
5—Very high

TABLE 7 (c)

COMPARISON OF MEAN SCORE FOR FEELING SEXUAL DESIRE

| Duration | Mean score (±std deviation) | |
|---|---|---|
| | Test product | Prior art Product |
| Pre-treatment | 3.00 | 3.00 |
| Week 4 | 6.80 | 5.25 |
| Week 8 | 7.00 | 6.30 |
| Week 12 | 8.15 | 7.35 |

Symptoms of Vaginal Infections Like Vaginal Itching, Vaginal Discharge, Odour, Inflammation, Burning Pain were Evaluated; However Results of Vaginal Itching are Provided Below:

The observations were graded as follows:

0—None
1—Mild
2—Moderate
3—Severe

TABLE 7 (d)

| Duration | Mean score (±std deviation) | |
|---|---|---|
| | Test product | Prior art Product |
| Pre-treatment | 2.21 | 2.15 |
| Week 4 | 1.08 | 1.42 |
| Week 8 | 0.53 | 1.09 |
| Week 12 | 0.24 | 0.70 |

CONCLUSION

Surprisingly, the herbal formulation of the present invention comprising of *Woodfordia floribunda* plant extract and *Centella asiatica* plant extract along with at least one pharmaceutically acceptable carrier or excipient was found to be more efficacious over the prior art product.

The efficacy parameters such as Vaginal Laxity/looseness; Sexual Satisfaction; Female Sexual Function Index; Symptoms of Vaginal Infections such as vaginal itching; vaginal discharge; odour; inflammation and burning pain were evaluated on the basis of ratings by the patients, which showed a significant results in the group treated with herbal formulation according to an embodiment of the invention [test product] than to the group treated with prior art product that showed very less results.

Further, the degree of improvement in terms of percentage improvement in vaginal laxity, sexual satisfaction, desire, arousal, lubrication, orgasm, overall satisfaction, pain, vaginal itching, vaginal discharge, odour, inflammation, burning pain; observed as per investigator and patient evaluation was 84%, 84%, 83%, 84%, 81%, 76%, 84%, 85%, 77%, 81%, 80%, 83% and 76% respectively in the test product group.

Significantly lesser improvement was observed in group treated with prior art product. Only group with test product showed significant improvement compared to initial value.

Also, there were no adverse reactions observed in the test product group and in the prior art product group.

Further, the safety of the composition was also evaluated and there were no adverse events observed during the study.

EXAMPLE 8

Efficacy Study of Individual Herbal Gel Formulation Vis-à-Vis Herbal Formulation Comprising Combination of *Woodfordia floribunda* Plant Extract and *Centella asiatica* Plant Extract was Evaluated Based on Similar Criteria Such as Vaginal Laxity/Looseness, Sexual Satisfaction and Vaginal Infection Herbal formulation comprising *Woodfordia floribunda* plant extracts (W1):

| Component | % w/w |
|---|---|
| *Woodfordia Floribunda* | 0.75 |
| *Punica Granatum* | 0.75 |
| Alovera | 1.5 |
| Almond | 1.5 |
| Alum | 0.5 |
| Vitamin E | 0.02 |
| Gold | 0.02 |
| Flavor | 0.02 |
| DM Water | 89 |

Herbal formulation comprising *Centella asiatica* plant extracts (C1):

| Component | % w/w |
|---|---|
| *Centella Asiatica* | 0.75 |
| *Punica Granatum* | 0.75 |
| Alovera | 1.5 |
| Almond | 1.5 |
| Alum | 0.5 |
| Vitamin E | 0.02 |
| Gold | 0.02 |
| Flavor | 0.02 |
| DM Water | 89 |

Herbal formulation comprising *Woodfordia floribunda* plant extract and *Centella asiatica* plant extract (F1):

| Component | % w/w |
|---|---|
| *Woodfordia Floribunda* | 0.75 |
| *Centella Asiatica* | 0.75 |
| *Punica Granatum* | 0 |
| Alovera | 1.5 |
| Almond | 1.5 |
| Alum | 0.5 |
| Vitamin E | 0.02 |
| Gold | 0.02 |
| Flavor | 0.02 |
| DM Water | 89 |

Comparative data of the herbal formulation indicating individual herbal ingredients (W1 & C1) vis-à-vis combination formulation (F1) in terms of vaginal laxity, sexual satisfaction and infections in female subjects at different stages of treatment:

TABLE 6

Effect of combination formulation (F1) vis-à-vis individual formulation (W1, C1) in terms of vaginal laxity at different stages:

| Stages | Placebo | W1 | C1 | F1 |
|---|---|---|---|---|
| Pre-Treatment | 2.22 | 2.25 | 2.30 | 2.28 |
| Week 4 | 2.17 | 2.51 | 3.48 | 3.53 |
| Week 8 | 2.38 | 2.70 | 2.72 | 2.80 |
| Week 12 | 2.41 | 3.40 | 3.30 | 4.00 |

It was observed that on week 4 after treatment in relation to the vaginal tightening, the individual composition of *Woodfordia floribunda* plant extract (W1) gave 2.25 index value i.e. it gave 0.34 higher index than the placebo (2.51−2.17=0.34); at 2 gms once a day this corresponds to 0.34/2=0.17 more; whereas individual composition of *Centella asiatica* plant extract (C1) gave 2.30 index value i.e. it gave 1.31 higher index than the placebo (3.48−2.17=0.34); at 2 gms once a day this corresponds to 1.31/2=0.65 more. Thus the sum of the index value of both individual composition amounts to 0.82 more (this will be expected additive effect of both individual composition). It was observed that on week 4 after treatment the formulation comprising both the active ingredients (F1) gave 2.28 index value which is 1.36 more than placebo (3.53−2.17=1.36). Thus, the result obtained showed enhanced synergy.

Similarly, the herbal formulation of the present invention comprising of *Woodfordia floribunda* plant extract and *Centella asiatica* plant extract along with pharmaceutically acceptable carriers or excipient showed enhanced effects till the end of the treatment i.e. week 8 (0.42 more) week 12 (1.59 more) when compared to the individual formulations (W1 and C1) using same calculation. In other words, though the individual formulation W1 and C1 were found to be of little effect in the treatment but the study results in Table 6 clearly indicate that the herbal formulation provided far better synergistic effect.

TABLE 7

Effect of combination formulation (F1) vis-à-vis individual formulation (W1, C1) in relation to sexual satisfaction

| Stages | Placebo | W1 | C1 | F1 |
|---|---|---|---|---|
| Pre-Treatment | 2.00 | 2.05 | 2.10 | 2.03 |
| Week 4 | 2.07 | 2.34 | 2.32 | 2.42 |
| Week 8 | 2.14 | 2.62 | 2.65 | 3.67 |
| Week 12 | 2.20 | 2.88 | 2.79 | 3.98 |

Surprisingly, the study demonstrated that the herbal formulation of present invention also provided high sexual satisfaction in female subjects compared to the individual formulation as evident from Table 7. The results when calculated using the calculation stated above clearly indicated that the combination formulation provides sexual satisfaction in higher degree when compared to their individual formulation; therefore the claimed herbal formulation is synergistic in nature.

TABLE 8

Effect of combination formulation (F1) vis-à-vis individual formulation (W1, C1) with respect to vaginal infection at different stages:

| Stages | Placebo | W1 | C1 | F1 |
|---|---|---|---|---|
| Pre-Treatment | 1.89 | 1.84 | 1.88 | 1.06 |
| Week 4 | 1.49 | 1.32 | 1.50 | 1.17 |
| Week 8 | 1.54 | 1.23 | 1.32 | 0.59 |
| Week 12 | 1.43 | 1.10 | 1.06 | 0.23 |

It was observed that on treatment with the herbal formulation of the present invention comprising of *Woodfordia floribunda* plant extract and *Centella asiatica* plant extract along with pharmaceutically acceptable carriers or excipient showed decrease in symptoms of vaginal infection at the end of the treatment i.e. week 12 as compared to the individual formulations (W1 and C1) as evident from Table 8. This again indicates that the herbal formulation of the present invention when calculated using the calculation stated above provides far better synergistic effect.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope and spirit of this invention.

I claim:

1. A herbal gel formulation for inter-vaginal application consisting of:
   a) a combination of a *Woodfordia floribunda* plant polar solvent extract in the range of 0.1% w/w to 5% w/w of the herbal gel formulation and a *Centella asiatica* plant polar solvent extract in the range of 0.1% w/w to 5% w/w of the herbal formulation, wherein the combination is in an effective amount to provide a treatment of vaginal conditions upon inter-vaginal application; and b) at least one pharmaceutically acceptable water-based excipient to formulate the gel, in the range of 90% w/w to 98% w/w of the herbal gel formulation.

2. The herbal gel formulation as claimed in claim 1, wherein the pharmaceutically acceptable excipient is selected from the group consisting of: astringent, antioxidant, vaginal conditioning agent, vasodilating agent, thickening agent, preservative, lubricating agent, vitality imparter, flavouring agents, colorant and water or combinations thereof, wherein said vitality imparter is selected from the group consisting of: gold, gold glitter and cold fine particles.

3. The herbal gel formulation as claimed in claim 2, wherein the pharmaceutically acceptable astringent is selected from the group consisting of: of Potassium Aluminum Sulphate (alum), extracts of *Punica granatum, Acacia senegal, Andrographis paniculata, Curcuma comosa, Aancyelus pyrethrum* (anar kara), Shilajit or combinations thereof, wherein the astringent is in the range of 0.01% w/w to 5% w/w of the formulation.

4. The herbal gel formulation as claimed in claim 2, wherein the antioxidant is selected from the group consisting of: of Vitamin E, Vitamin C, gold nanoparticles or combinations thereof, wherein the antioxidant is in the range of 0.01% w/w to 5% w/w of the formulation.

5. The herbal gel formulation as claimed in claim 2, wherein the vaginal conditioning agent is selected from the group consisting of: Aloe vera, almond extract, propylene glycol, *Aloe* barbadensis, *Tinospora cordifolia*, Shilajit, glycols, glycerine, and sorbitol or combinations thereof, wherein the vaginal conditioning agent is in the range of 0.5% w/w to 5% w/w of the formulation.

6. The herbal gel formulation as claimed in claim 2, wherein the vasodilating agent is an extract of a plant selected from the group consisting of *Butea frondosa, Myristica fragrans, Asparagus racemosus, Butea monosperma, Acorus callomus, Withinia somnifera*, and combinations thereof, wherein the vasodilating agent ranges from 1% w/w to 5% w/w of the total formulation.

7. The synergistic herbal gel formulation a claimed in claim 2, wherein the thickening agent is selected from the group consisting of: carbomer, sodium carboxymethylcellulose, and gelatin or combinations thereof, wherein the thickening anent is in the range of 0.5% w/w 5% w/w of the total composition.

8. The herbal gel formulation as claimed in claim 7, wherein the preservative is selected from the group consisting of: sodium benzoate, potassium cordate, sodium methyl paraben, propyl paraben, benzoic acid, sodium metabisulfite, disodium EDTA, butyl paraben, and chlorobutanol or combinations thereof and wherein the preservative is in the range of 0.01% w/w to 2.0% w/w of the formulation.

9. The herbal gel formulation as claimed in claim 2, wherein the lubricating agent is selected from the group consisting of: sesame oil, propylene glycol, and almond oil or combinations thereof and wherein the lubrication agent is in the range of 0.01% w/w to 5% w/w of the formulation.

10. The herbal gel formulation as claimed in claim 2, wherein the vitality imparter is in the range of 0.01% w/w to 0.05% w/w of the formulation.

11. The herbal gel formulation a claimed in claim 2, wherein the flavouring agent is selected from the group consisting of: apricot, vanilla, cane berry, green apple, almond, honey and rose or combinations thereof; and wherein the flavoring agent is in the range of 0.01% w/w to 0.05% w/w of the formulation.

12. The herbal gel formulation as claimed in claim 2 wherein the colorant is of a gold colour, and wherein the colorant is in the range of 0.01% w/w to 0.04% w/w of the formulation.

13. A herbal gel formulation for inter-vaginal application consisting essentially of:
a) a combination of a *Woodfordia foribunda* plant polar solvent extract in the amount of 0.1% w/w to 5% w/w of the herbal gel formulation and a *Centella asiatica* plant polar solvent extract in the amount of 0.1% w/w to 5% w/w of the herbal formulation wherein the combination is in an effective amount to provide a treatment of vaginal conditions upon inter-vaginal application;
b) Carbomer in the amount of 0.5% w/w to 1.5% w/w of the herbal gel formulation;
c) Propylene glycol in the amount of 0.01% w/w to 5% w/w of the herbal gel formulation: and
d) a sufficient amount of water to form a gel.

* * * * *